(12) United States Patent
Rodriguez et al.

(10) Patent No.: US 10,383,617 B2
(45) Date of Patent: Aug. 20, 2019

(54) GRAFT SUSPENSION DEVICE

(71) Applicant: Smith & Nephew, Inc., Memphis, TN (US)

(72) Inventors: Christopher Michael Rodriguez, Costa Mesa, CA (US); Norman Gordon, Irvine, CA (US); Tri Nguyen, Garden Grove, CA (US); Stephen Santangelo, Sturbridge, MA (US)

(73) Assignee: Smith & Nephew, Inc., Memphis, TN (US)

( * ) Notice: Subject to any disclaimer, the term of this patent is extended or adjusted under 35 U.S.C. 154(b) by 74 days.

(21) Appl. No.: 15/431,927

(22) Filed: Feb. 14, 2017

(65) Prior Publication Data

US 2017/0231752 A1    Aug. 17, 2017

Related U.S. Application Data

(60) Provisional application No. 62/295,791, filed on Feb. 16, 2016.

(51) Int. Cl.
*A61B 17/04* (2006.01)
*A61F 2/08* (2006.01)
*A61B 17/06* (2006.01)

(52) U.S. Cl.
CPC .. *A61B 17/0401* (2013.01); *A61B 2017/0404* (2013.01); *A61B 2017/0414* (2013.01); *A61B 2017/0417* (2013.01); *A61B 2017/06185* (2013.01); *A61F 2/0811* (2013.01); *A61F 2002/0817* (2013.01); *A61F 2002/0852* (2013.01)

(58) Field of Classification Search
CPC ............... A61B 17/0401; A61F 2/0811; A61F 2002/0852; A61F 2002/0817
See application file for complete search history.

(56) References Cited

U.S. PATENT DOCUMENTS

| 5,041,118 A | 8/1991 | Wasilewski |
| 5,507,812 A | 4/1996 | Moore |
| 6,517,542 B1 | 2/2003 | Byerman |

(Continued)

FOREIGN PATENT DOCUMENTS

| BR | 102014018974 A2 | 9/2015 |
| EP | 2238944 A2 | 10/2010 |

(Continued)

OTHER PUBLICATIONS

International Search Report and Written Opinion dated May 15, 2017, in Application No. PCT/US2017/017774.

(Continued)

*Primary Examiner* — Bruce E Snow
*Assistant Examiner* — Melissa A Hoban
(74) *Attorney, Agent, or Firm* — Norman F. Hainer, Jr.

(57) ABSTRACT

A graft suspension device for suspending a ligament in a bone hole having a first loop and a second loop suspending from an 8-hole anchor, and a cradle at the opposite end of the loops to the anchor. The loose ends of the suture are routed through holes in the anchor separate from the loops and are joined together to form a single tail. A finger loop allows a surgeon to adjust the distance of the cradle from the anchor with the cradle staying centered with respect to the anchor as the distance is adjusted.

23 Claims, 8 Drawing Sheets

(56) References Cited

U.S. PATENT DOCUMENTS

| | | |
|---|---|---|
| 6,517,578 B2 | 2/2003 | Hein |
| 6,554,862 B2 | 4/2003 | Overaker |
| 7,601,155 B2 | 10/2009 | Petersen |
| 8,460,379 B2 | 6/2013 | Albertorio et al. |
| 8,652,172 B2 * | 2/2014 | Denham ............ A61B 17/0401 606/228 |
| 8,753,375 B2 | 6/2014 | Albertorio |
| 2001/0041938 A1 | 11/2001 | Hein |
| 2002/0156476 A1 | 10/2002 | Wilford |
| 2003/0065361 A1 | 4/2003 | Dreyfuss |
| 2005/0234463 A1 | 10/2005 | Parcher |
| 2006/0190041 A1 | 8/2006 | Fallin |
| 2007/0005069 A1 | 1/2007 | Contiliano |
| 2009/0043342 A1 | 2/2009 | Freedland |
| 2009/0234387 A1 | 9/2009 | Morales |
| 2010/0160962 A1 * | 6/2010 | Dreyfuss ............ A61B 17/0401 606/228 |
| 2011/0087280 A1 | 4/2011 | Albertorio |
| 2011/0224729 A1 * | 9/2011 | Baker ................ A61B 17/0401 606/232 |
| 2012/0095470 A1 | 4/2012 | Stone |
| 2013/0096612 A1 | 4/2013 | Zajac et al. |
| 2013/0197580 A1 | 8/2013 | Periello et al. |
| 2013/0268073 A1 | 10/2013 | Albertorio et al. |
| 2014/0074239 A1 | 3/2014 | Albertorio et al. |
| 2015/0039026 A1 | 2/2015 | Pasquali et al. |
| 2015/0057750 A1 | 2/2015 | Timmerman |
| 2015/0157449 A1 | 6/2015 | Gustafson et al. |
| 2015/0201929 A1 | 7/2015 | Dooney, Jr. et al. |

FOREIGN PATENT DOCUMENTS

| | | |
|---|---|---|
| RU | 2017469 C1 | 8/1994 |
| RU | 2289361 C1 | 12/2006 |
| WO | 2010121302 A1 | 10/2010 |
| WO | 2012056384 A2 | 5/2012 |

OTHER PUBLICATIONS

AU Office Action for App No. 2013280421 dated Sep. 9, 2017, 3 pages.

JP Office Action for App No. 2014-555727 dated Jun. 26, 2017, 3 pages.

RU Office Action for App No. 2015101568 dated May 23, 2017, 9 pages.

European Application No. 17706389.8-1122 Office Action dated Sep. 27, 2018.

* cited by examiner

GRAFT SUSPENSION DEVICE

CROSS-REFERENCE TO RELATED APPLICATIONS

This application claims priority to and benefit of U.S. Provisional Application No. 62/295,791, filed on Feb. 16, 2016, the contents of which are incorporated by reference herein in their entirety for all purposes.

FIELD

The present disclosure relates to a graft suspension device and, in particular, a graft suspension device for graft fixation such as tendon or ligament fixation.

BACKGROUND OF THE DISCLOSURE

Sports injuries are increasingly common, such as when tissues such as ligaments or tendons tear or detach from bone. Surgical techniques have been developed to reconstruct such soft tissues and to re-attach them to the relevant bone. One of the most common types of such injuries is the tearing of the anterior cruciate ligament (ACL) in the knee. The ACL connects the femur to the tibia at the center of the knee joint. Reconstruction of such tissues generally involves replacement with a graft, such as autologous or artificial tendon.

One method of graft fixation within the femoral tunnel involves the use of a fixation device on the anterolateral femoral cortex which is attached to the graft by means of sutures or tapes. The ligament anchor may be threaded through a femoral tunnel formed through the femur from the center of the knee. Sutures are attached directly to the fixation device on the outside of the femur above the knee the graft is looped through the suture before passing out of the femoral tunnel and being secured to the tibia.

One particularly important issue in the grafting operation is the formation of the suture loop attached to the fixation device, over which the graft is passed. Rigid suture loops require that the end surgeon have an inventory of multiple sizes of rigid loops depending on the size of the bone tunnel. Rigid loops also require an extra 3-5 mm of tunnel depth in order to maneuver the fixation device during the surgical procedure. Adjustable loops, on the other hand, require movement of the suture loop around the fixation device, causing abrasion to the attached graft. Concerns about adjustable loops inadvertently lengthening after graft fixation also exist.

SUMMARY OF THE DISCLOSURE

Described herein is a graft suspension device for a ligament fixation graft comprising an anchor or cortical button at one end, a ligament cradle at the other end and an adjustable length of suture therebetween, the suture formed into at least two loops engaging the anchor. A cradle at the midpoint of the suture comprises a sleeve portion through which the ends of the suture are threaded in opposite directions to cross-over in the sleeve portion and emerge at opposite ends of the sleeve portion. The ends of the suture are then routed through apertures in the anchor separate from the routing of the suture loops. Finally, the two ends of the suture are joined together to form a single tail. The size of the loops may be changed as the single tail is manipulated. However, the cradle stays centered on the suture even while the size of the loops change. This lack of cradle movement advantageously eliminates relative motion of the suture to the graft, which may weaken or cut the graft. The single tail, moreover, allows a surgeon to reduce the size of the loop with one hand.

Further examples of the graft suspension device of this disclosure may include one or more of the following, in any suitable combination.

In one example, the graft suspension device includes a suspension means for suspending a ligament in a bone hole. The suspension means includes an anchoring means at one end. The anchoring means has an anchor having a proximal end, a distal end, and a longitudinal axis extending between the proximal and distal ends. The anchor further has an outer pair, an intermediate pair and two central pairs of apertures configured for passage of a suture. The outer pair and the intermediate pair of apertures are aligned along the longitudinal axis, and the two central pairs of apertures are offset from the longitudinal axis but aligned with each other transverse to the longitudinal axis. The suspension means also includes a cradling means at the opposite end from the anchoring means, and an adjustable length of suture between the anchoring means and the cradling means. The suture is formed into at least two loops engaging the two central pairs of apertures of the anchor. The cradling means includes a sleeve portion though which first and second ends of at least a first of the at least two loops are threaded in opposite directions to cross over in the sleeve portion and emerge at opposite ends of the sleeve portion. The first and second ends of the suture are then passed through separate ones of the intermediate pair of apertures and joined together to form a single tail. Manipulation of the single tail changes the size of the at least two loops. The sleeve portion remains centered with respect to the anchor when the size of the at least two loops is reduced.

In further examples, the single tail is formed from the first end of the suture being spliced within the second end of the suture, and the second end of the suture being spliced within the first end of the suture. The single tail is adapted to include a gripping element. The suture is formed from a plurality of threads, the threads being plaited together to form a hollow tubular structure. A length of the adjustable length of suture is about 46 inches. A length of the anchor is about 10 mm to about 15 mm and a width of the anchor is about 2 mm to about 5 mm. The graft suspension device further includes at least one ligament graft engaged with the cradling means. The sleeve portion forms an integral part of a second of the at least two loops. The sleeve portion includes first and second openings formed in a second of the at least two loops at spaced intervals through which the first and second ends of the suture are threaded. A length of the sleeve portion is selected to be long enough accommodate a ligament fixation graft suspended thereover, but short enough to facilitate adjustment of at least one of the at least two loops. A diameter of the intermediate pair of apertures is selected to be larger than a diameter of the outer and inner pairs of apertures.

An example of the method of forming a graft suspension device includes threading first and second ends of a suture through respective first apertures of a central pair of apertures from an underside to a top side of an anchor, the suture forming at least two loops; threading the first and second ends of the suture through respective second apertures of the central pair of apertures from the top side to the underside of the anchor; threading the first and second ends in opposite directions through a sleeve portion formed in a cradle of the suture; threading the first and second ends of the suture through respective first and second apertures of an intermediate pair of apertures from an underside to the top side of the anchor; and joining the first and second ends of the suture together to form a single tail. The single tail is adapted to include a gripping element. When the single tail is pulled away from the anchor in an opposite direction from the cradle, a length of at least one of the at least two loops is shortened. As a length of the at least one of the at least two loops is shortened, the cradle remains centered with respect to the anchor. Joining the first and second ends of the suture together includes splicing the first end of the suture within the second end of the suture, and splicing the second end of the suture within the first end of the suture. Release of the single tail after the length of the at least one of the at least two loops is shortened does not cause the at least one of the at least two loops to re-lengthen.

BRIEF DESCRIPTION OF THE DRAWINGS

Embodiments of the disclosure will now be described by way of example, with reference to the accompanying drawings in which.

DETAILED DESCRIPTION

Figure 1A:
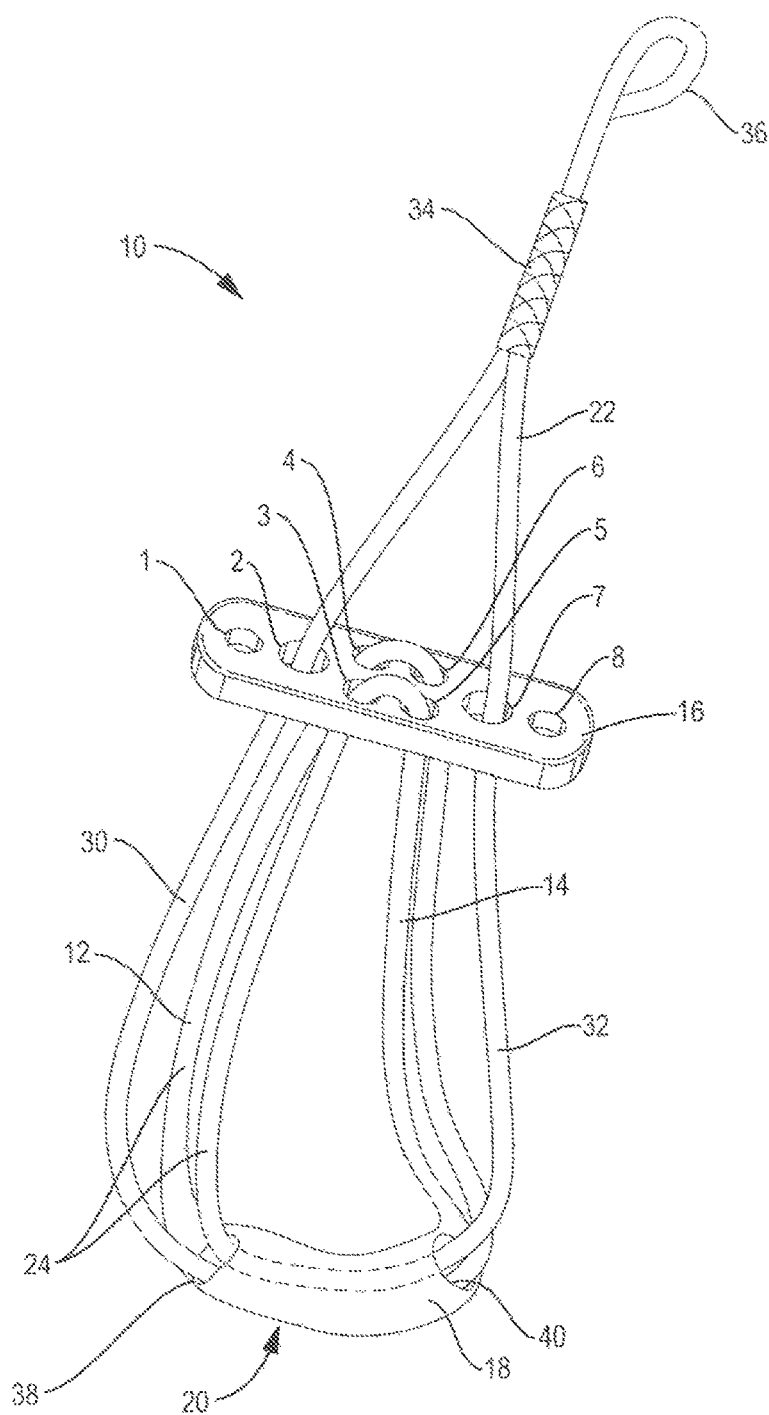
FIG. 1A shows a graft suspension device in accordance with the present disclosure.

The foregoing and other features will be apparent from the following description of particular embodiments disclosed herein, as illustrated in the accompanying drawings.

In the description that follows, like components have been given the same reference numerals, regardless of whether they are shown in different examples. To illustrate an example(s) of the present invention in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

Comprise, include, and/or plural forms of each are open ended and include the listed parts and can include additional parts that are not listed. And/or is open ended and includes one or more of the listed parts and combinations of the listed parts.

Referring now to FIG. 1A, an example of the graft suspension device 10 of this disclosure is shown. The graft suspension device 10 comprises a strand of suture 22 having a first loop 12 and a second loop 14 (together, the suspension loop 24) suspended from an anchor 16. The suture 22 is formed from a braided material having plaited threads which together form a hollow tubular material. The suture 22 may be made from a suitable bio-compatible material which may be a bio-absorbable material or a non-absorbable permanent material. A length of the strand of suture 22 may be about 46 inches. The anchor 16 may be of conventional construction for securement to the outside of a bone, such as a cortical button. A length of the anchor (or cortical button) 16 may be about 10 mm to about 15 mm and a width may be about 2 mm to about 5 mm. The graft suspension device 10 also has a cradle 20 located substantially midway along the length of the suture 22, as further described below. The cradle 20 includes a sleeve portion 18 at the opposite end of the suspension loop 24 to the anchor 16, as further described below.

Figure 1B:
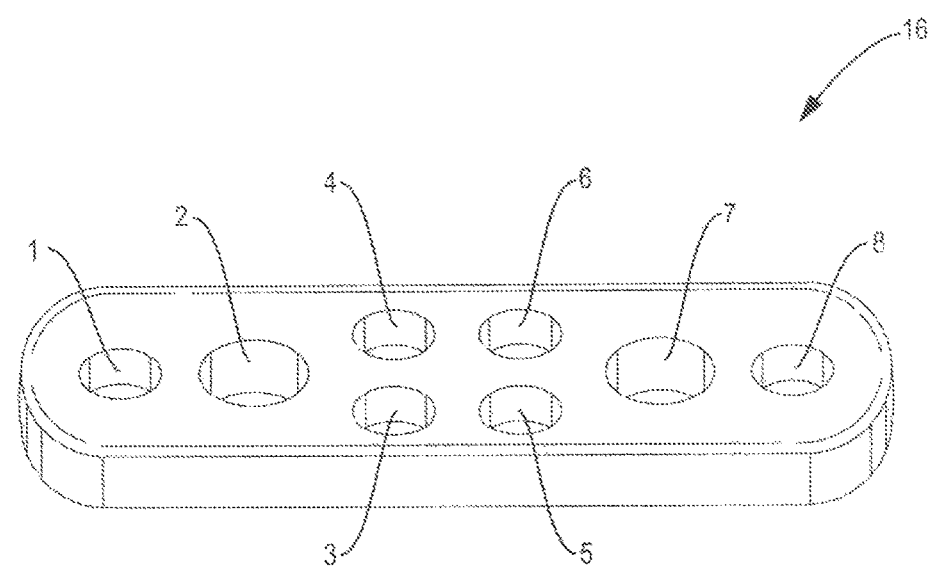
FIG. 1B shows a detail of the anchor of FIG. 1A.

As further shown in FIG. 1A, the anchor 16 includes a plurality of apertures, which may be eight apertures, extending therethrough and configured for the passage of the suture 22 (see, also, FIG. 1B). Outer and intermediate apertures 1, 2, 7 and 8 are aligned with each other along the longitudinal axis of the anchor 16. Central apertures 3, 4, 5 and 6 are formed in two pairs symmetrically offset from the longitudinal axis but aligned with each other transverse to the longitudinal axis. The two pairs of central apertures 3, 4, 5, 6 are designed to accommodate the suture loops 12, 14 therethrough. The intermediate pair of apertures 2, 7 are designed to accommodate the two ends 30, 32 of the suture respectively. The outer pair of apertures 1, 8 are designed to assist in the placement of the anchor 16 on the outside of a bone through the use of leading and trailing sutures passed through apertures 1, 8 (not shown). A diameter of the intermediate pair of apertures 2, 7 may be selected to be larger than a diameter of the apertures 1, 3, 4, 5, 6, and 8. First and second loops 12, 14 are shown threaded through the central apertures 3, 4, 5, 6 as further described below. The loose ends 30, 32 of the suture 22 are shown threaded through the sleeve portion 18 to complete the suspension loop 24. The threading of the loose ends 30, 32 in this manner has the effect of widening the sleeve portion 18 with respect to the remainder of the suspension loop 24. The loose ends 30, 32 are then shown as passing through the intermediate pair of apertures 2, 7 and joined together to form a single tail 34, as further described below. Advantageously, routing the suture 22 through the plurality of apertures keeps the various strands of suture 22 separated, making them less likely to bunch or tangle. The single tail 34 may be further adapted to form a finger loop 36 to provide a means whereby the surgeon can adjust the distance of the cradle 18 from the anchor 16, and/or shortening the length of the suspension loop 24, either before or during the surgical operation. Advantageously, the finger loop 36 may be used with just one hand.

Figure 1C:
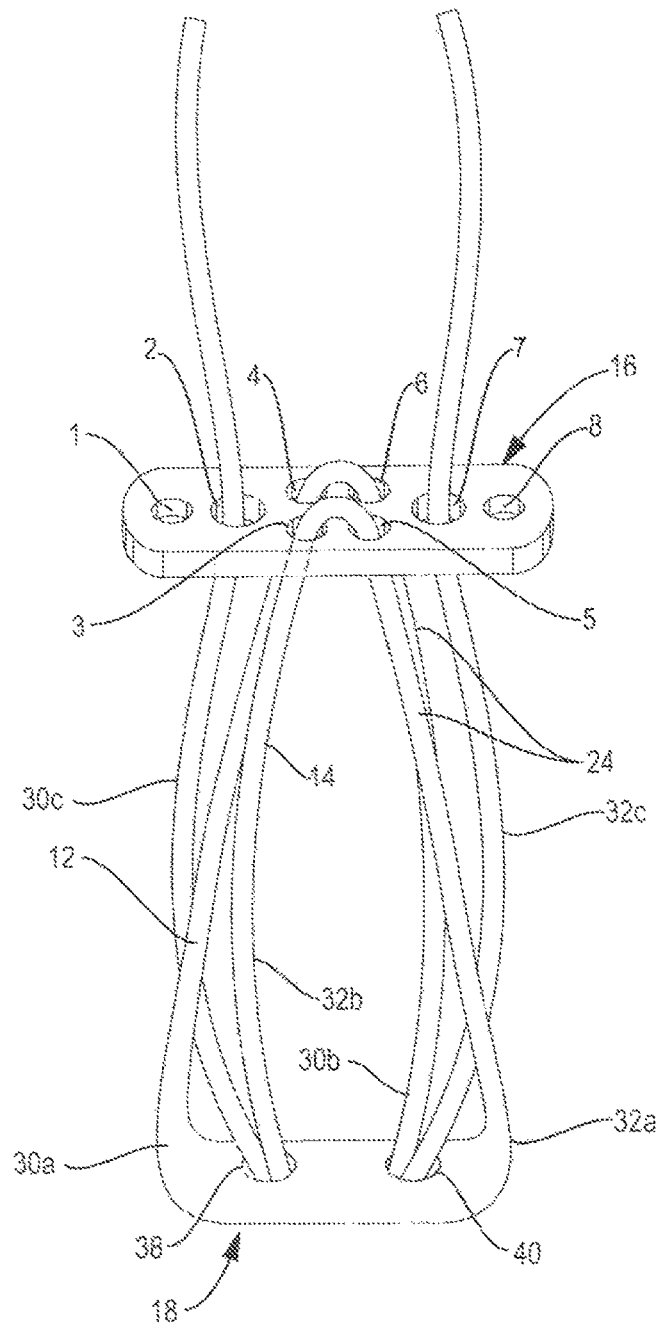
FIG. 1C is a schematic of the method of forming the suspension loop of FIG. 1A.

As shown in FIG. 1C, the sleeve portion 18 forms an integral part of the first and second loop 12, 14. First and second eyes 38, 40 are formed in the sleeve portion 18 at spaced intervals through which the loose ends 30, 32 may be threaded, as further described below. It is contemplated by this disclosure that first and second eyes 38, 40 need not be formed in the sleeve portion 18 if the loose ends 30, 32 may be threaded therethrough by passing through gaps between adjacent threads of the braided suture 22. A length of the sleeve portion 18 can vary, but is selected to be sufficiently long enough to accommodate a ligament fixation graft suspended thereover, but short enough to facilitate efficient adjustment of the suspension loop 24.

Still referring to FIG. 1C, forming the first and second loops 12, 14 involves threading the loose ends 30, 32 through a respective pair of central apertures 3, 4, 5, 6 of the anchor 16 from the underside to the top side thereof. More particularly, loose end portion 30a is threaded through central aperture 4 and loose end portion 32a is threaded through central aperture 5. Each of the loose end portions 30a, 32a are then looped back through the other of the pair of apertures 6, 3 adjacent to the aperture through which it has already been passed. Specifically, the loose end portion 32b passes through aperture 3 from the top side to the underside of the anchor 16, and loose end portion 30b passes through aperture 6 from the top side to the underside of the anchor 16. Thereafter, loose end portion 30b is threaded through cradle portion 18 entering aperture 40 and exiting aperture 38. Likewise, loose end portion 32b is threaded through the cradle 18 in the opposite direction, entering aperture 38 and exiting aperture 40. At this stage, each loose end portion 30c, 32c is passed through the intermediate pair of apertures 2, 7, from the underside of the anchor to the top side thereof, i.e., loose end portion 30c is passed through aperture 2 and loose end portion 32c is passed through aperture 7. The loose end portions 30c, 32c are then joined together to form the single tail 34 (FIG. 1A) on the side of the anchor opposite from the cradle.

Figure 2A:
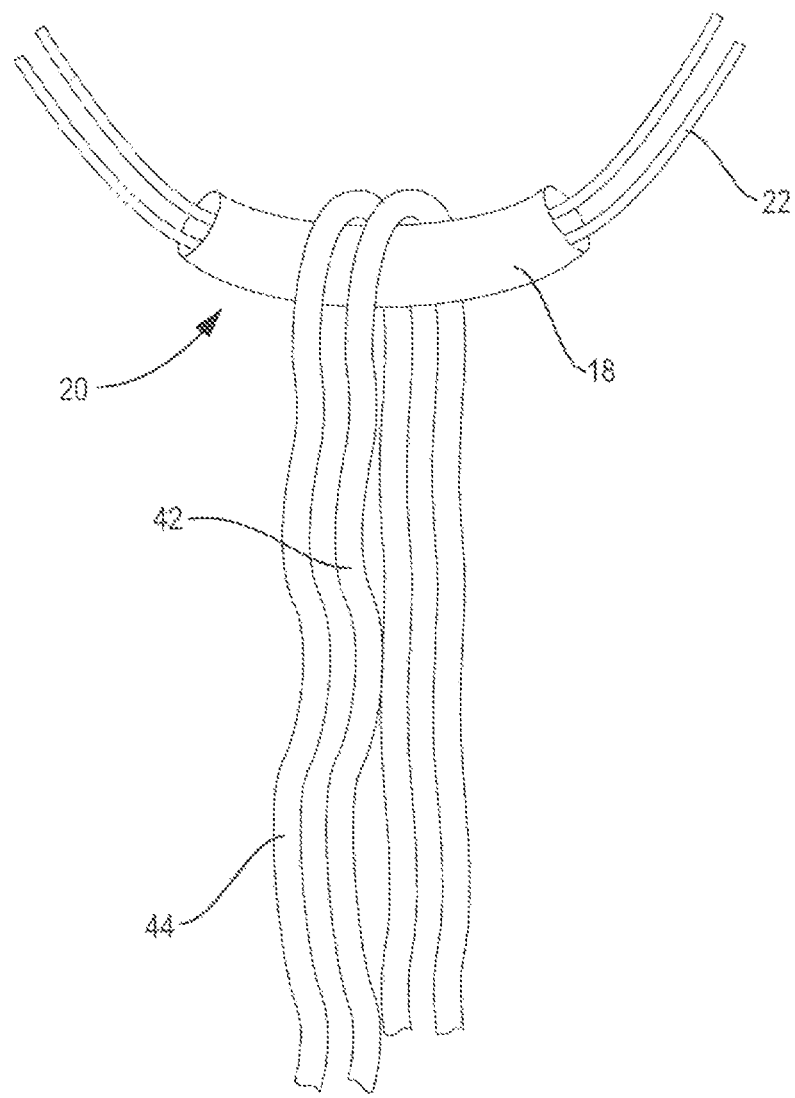
FIG. 2A shows a graft suspended over the cradle portion of a suspension loop in accordance with the present disclosure.
Figure 2B:
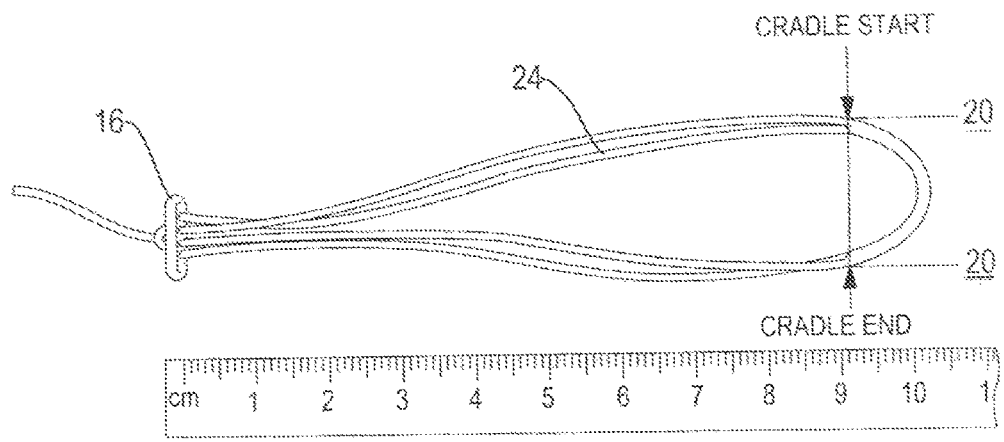
FIGS. 2B and 2C demonstrate a shortening of the suspension loop of FIG. 1A.
Figure 2C:
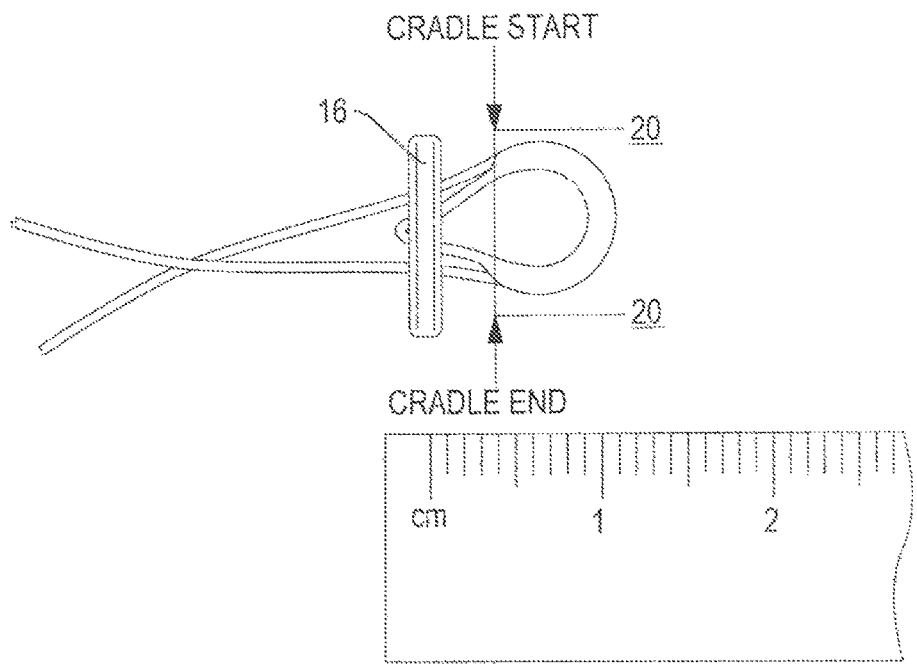

In FIG. 2A, a pair of ligament grafts 42, 44 are shown looped over the cradle 20 midway along the length thereof. Examples of grafts for use in the disclosure include ligament or tendon, in particular, reconstructed ligament or tendon. Advantageously, the wider sleeve portion 18 prevents the suture 22 from cutting into the grafts 42, 44 during the grafting process. Additionally, by pulling on the single tail 34 (FIG. 1) to shorten the length of the suspension loop 24, the cradle 20 remains centered with respect to the anchor 16, thus further preventing abrasion of the grafts 42, 44. For example, as shown in FIGS. 2B and 2C, the suspension loop 24 may be shortened from about 100 mm to about 8-10 mm (or to lengths therebetween) without the cradle 20 moving from a centered position with respect to the anchor 16.

Figure 3A:
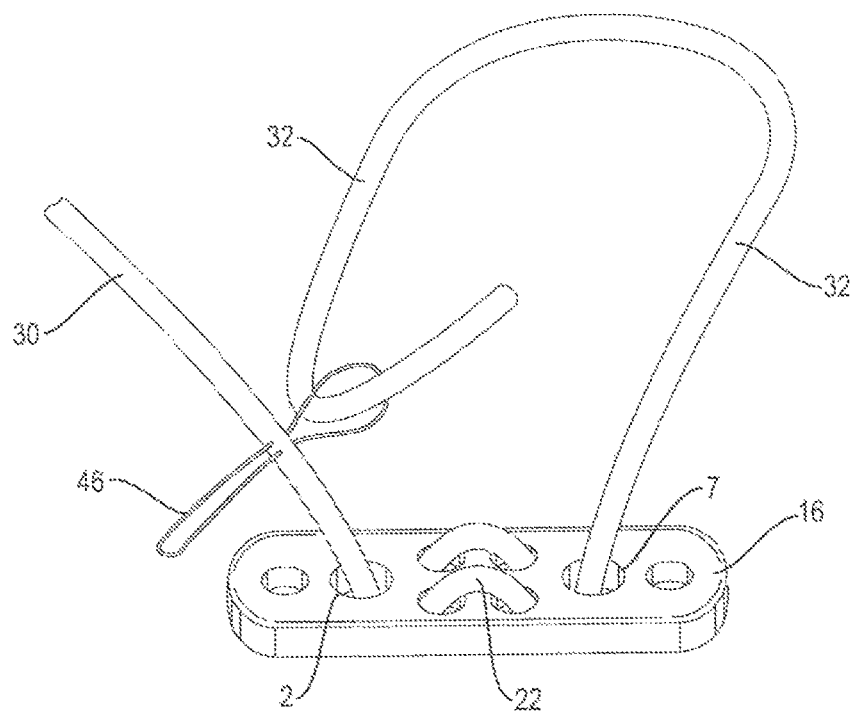
FIGS. 3A-D show a method of splicing the suture ends in accordance with the present disclosure.
Figure 3B:
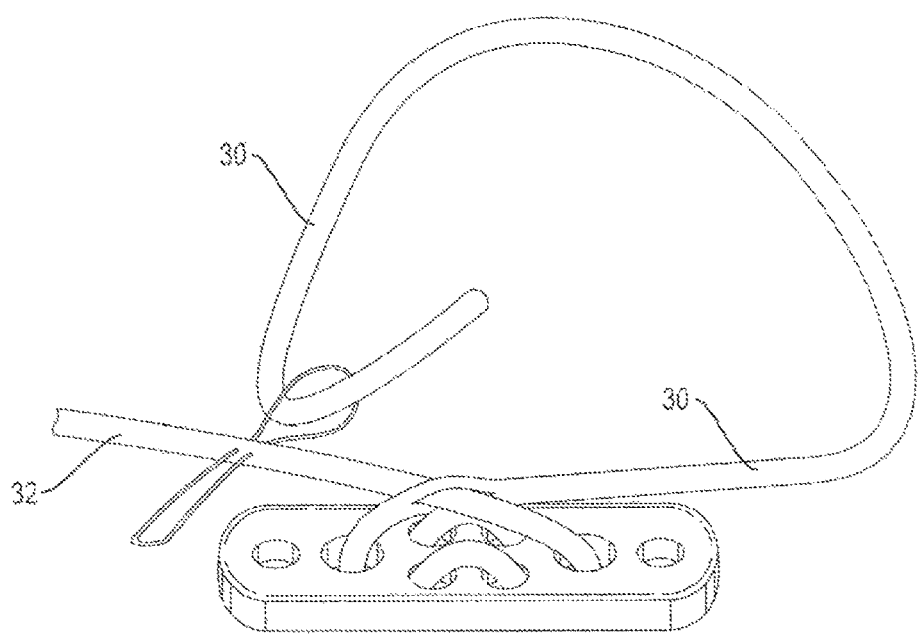

FIGS. 3A-D detail a method of joining loose ends 30, 32 together to form the single tail 34. FIG. 3A shows the loose ends 30, 32 passed through apertures 2, 7 on the opposite side of the anchor 16 from the cradle 20 (not shown). As shown in FIG. 3A, loose end 32 is captured through loose end 30 by means of a snaring tool 46 or other suitable tool. A shown in FIG. 3B, loose end 30 is subsequently snared through loose end 32. Advantageously, this reciprocity in splicing provides that, when the single tail 34 is pulled, loose ends 30, 32 do not slip relative to each other. This prevents the cradle 20 from moving from a centered position with respect to the anchor 16. It is also contemplated by this disclosure that the loose ends 30, 32 may be joined together to form a single tail 34 by other means, as long as loose ends 30, 32 do not slip relative to each other when the single tail 34 is pulled.

Figure 3C:
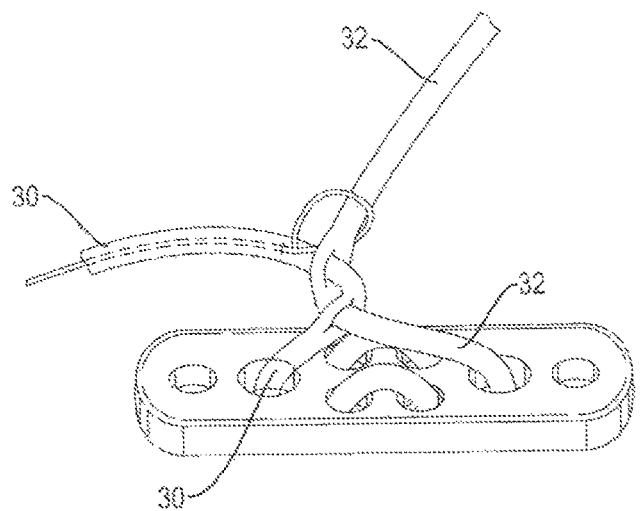
Figure 3D:
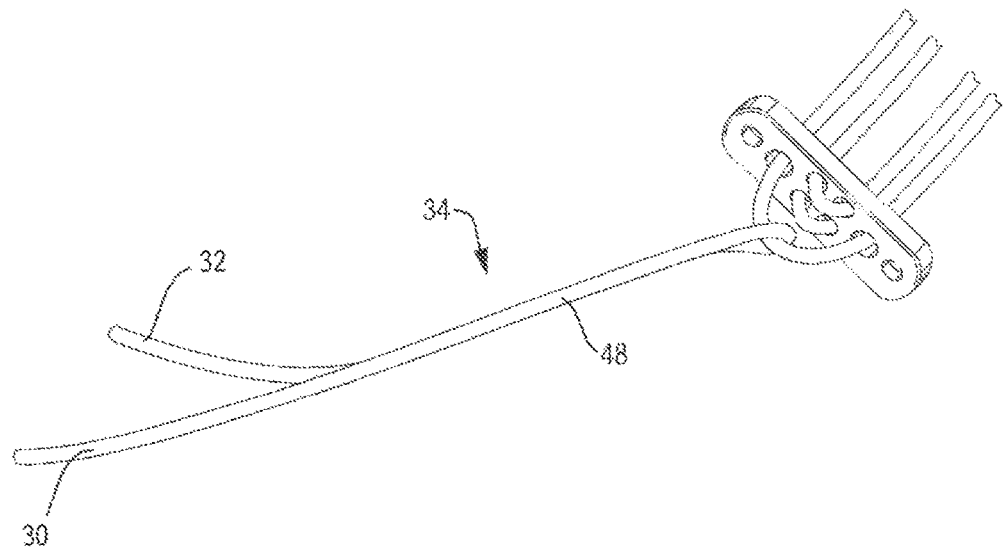

As shown in FIG. 3C, optionally, loose end 32 may be further ensnared inside a lumen of loose end 30. As shown in FIG. 3D, loose end 32 is pulled inside loose end 30, and is then trimmed flush to the spliced portion 48. In this way, the spliced loose ends 30, 32 form the entire length of the spliced portion 48, for greater pulling strength. The length of the single tail 34 is selected to be of sufficient length to pass out through an entrance of a bone tunnel to allow the surgeon to tension the grafts 42, 44 (FIG. 2A) or to simply adjust the length of the suspension loop 24 by pulling on the single tail 34. This allows for ease of tensioning and loop length adjustment both pre-operatively and/or intra-operatively.

Figure 4A:
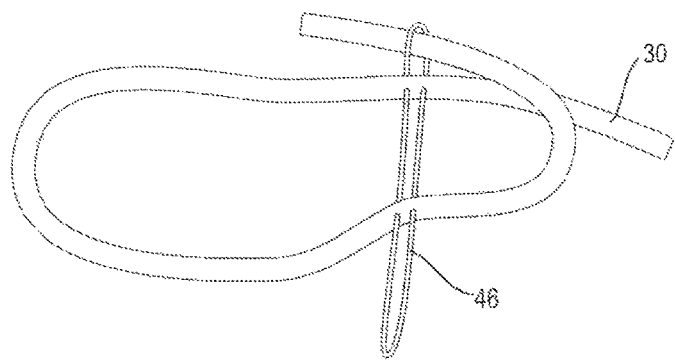
FIGS. 4A-C show a method of forming a finger loop in accordance with the present disclosure.
Figure 4B:
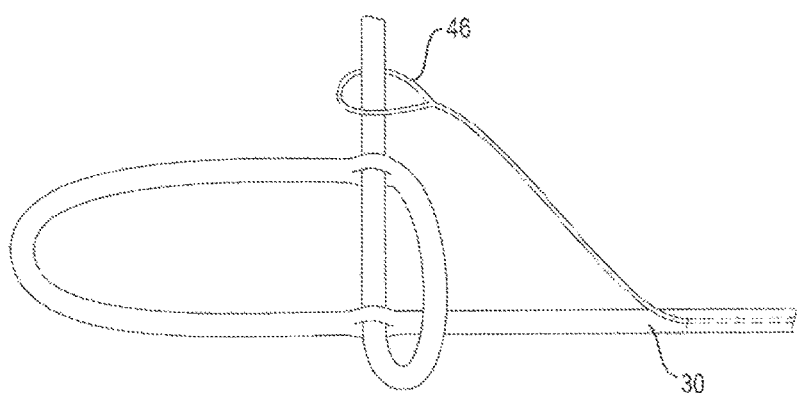
Figure 4C:
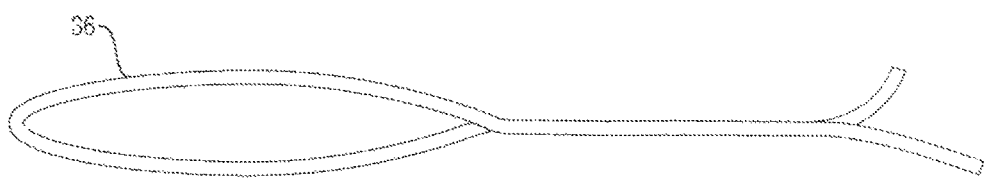

FIGS. 4A-C show a method for forming finger loop 36. To form the finger loop 36, the suture snare 46 is placed through remaining loose end 30 at two locations. The loose end 30 is then pulled through itself. The snaring tool 46 is then placed inside the lumen of loose end 30 and the loose end 30 is pulled inside to create the finger loop 36. By moving the finger loop 36 away from the cradle portion 18, the length of the suspension loop 24 is shortened and, in this manner, the tensioning of the grafts 42, 44 (FIG. 2A) may take place. Advantageously, release of the finger loop 36 after shortening does not cause the suspension loop 24 to re-lengthen. Therefore, the surgeon can adjust the grafts 42, 44 to the required tension and then tie-off subsequently, without the tension of the grafts 42, 44 being significantly lost in the intervening period.

While the system, apparatus and methods defined herein have been particularly shown and described with references to embodiments thereof, it will be understood by those skilled in the art that various changes in form and details may be made therein without departing from the scope of the invention encompassed by the appended claims.

What is claimed is:

1. A graft suspension device comprising suspension means for suspending a ligament in a bone hole, the suspension means comprising:
    an anchoring means at one end thereof, the anchoring means comprising an anchor having a proximal end, a distal end, and a longitudinal axis extending between the proximal and distal ends, the anchor further comprising an outer pair, an intermediate pair and two central pairs of apertures configured for passage of a suture, the outer pair and the intermediate pair of apertures being aligned along the longitudinal axis, and the two central pairs of apertures being offset from the longitudinal axis but aligned with each other transverse to the longitudinal axis;
    a cradling means at the other end thereof; and
    an adjustable length of suture therebetween, the suture being formed into a first and a second loop, engaging the two central pairs of apertures of the anchor;
    wherein the cradling means defines a sleeve portion through which first and second ends of the suture are threaded in opposite directions to cross over each other in the sleeve portion and emerge at opposite ends of the sleeve portion; and
    wherein the first and second ends of the suture are passed through separate ones of the intermediate pair of apertures and joined together to form a single tail.

2. The graft suspension device of claim 1, wherein manipulation of the single tail changes the size of at least one of the first and second loops.

3. The graft suspension device according to claim 2, wherein the single tail is configured such that the first and second ends of the suture do not slip relative to each other when the single tail is manipulated.

4. The graft suspension device of claim 1, wherein the sleeve portion remains centered with respect to the anchor when the single tail is manipulated.

5. The graft suspension device of claim 1, wherein the single tail terminates in a finger loop.

6. The graft suspension device of claim 1, wherein the suture comprises a plurality of threads, the threads being plaited together to form a hollow tubular structure.

7. The graft suspension device of claim 1, wherein a diameter of the intermediate pair of apertures is selected to be larger than a diameter of the outer and central pairs of apertures.

8. The graft suspension device of claim 1, wherein a length of the adjustable length of suture is about 46 inches.

9. The graft suspension device of claim 1, wherein a length of the anchor is about 10 mm to about 15 mm.

10. The graft suspension device of claim 1, wherein a width of the anchor is about 2 mm to about 5 mm.

11. The graft suspension device of claim 1, further comprising at least one ligament graft engaged with the cradling means.

12. The graft suspension device of claim 1, wherein the single tail comprises the first end of the suture spliced within the second end of the suture, and the second end of the suture spliced within the first end of the suture.

13. The graft suspension device of claim 1, wherein the sleeve portion forms an integral part of at least one of the loops.

14. The graft suspension device of claim 1, wherein the sleeve portion comprises first and second openings at spaced intervals through which the first and second ends of the suture are threaded.

15. The graft suspension device of claim 1, wherein a length of the sleeve portion is selected to be long enough to accommodate a ligament fixation graft suspended thereover, but short enough to facilitate adjustment of at least one of the first and second loops.

16. The graft suspension device of claim 1, wherein the anchor defines a cortical button, configured to engage an outer surface of bone.

17. The graft suspension device of claim 1, wherein the single tail is formed by capturing the first suture end through the second suture end, followed by capturing the second suture end through the first suture end, followed by ensnaring the first suture end inside and along a lumen of the second suture end.

18. A graft suspension device comprising a suspension means for suspending a ligament in a bone hole, the suspension means comprising:
- an anchoring means at one end thereof, the anchoring means comprising an anchor having an outer pair, an intermediate pair and two central pairs of apertures through a thickness of the anchor, the apertures all configured for passage of a suture, the outer pair and the intermediate pair of apertures being aligned along a central axis of the anchor, and the two central pairs of apertures offset from the central axis;
- a cradling means at the other end thereof; and
- an adjustable length of suture therebetween, the suture extending through the two central pairs of apertures so as to form a first and a second suture loop;
- wherein the cradling means comprises a sleeve portion through which first and second ends of the suture are threaded in opposite directions to cross over each other in the sleeve portion and emerge at opposite ends of the sleeve portion; and
- wherein the first and second ends of the suture are passed through separate ones of the intermediate pair of apertures and joined together to form a single tail.

19. The graft suspension device according to claim 18, wherein the central pairs of apertures are configured to keep the suture loops separated, to reduce tangling.

20. The graft suspension device according to claim 18, wherein the single tail is configured such that pulling on the single tail shortens at least one of the suture loops while maintaining a centered cradle with respect to the anchor.

21. The graft suspension device according to claim 18, wherein the single tail is formed by splicing the first and second ends reciprocally, so that first and second ends do not slip relative to each other when the single tail is pulled.

22. The graft suspension device according to claim 18, wherein the single tail further comprises a finger loop.

23. A graft suspension device for suspending a ligament within a bone hole comprising:
- an anchor having a first outer surface and a second outer surface defining a thickness of the anchor, the anchor also having an intermediate pair and two central pairs of apertures through the thickness of the anchor, the apertures all configured for passage of a suture through the thickness of the anchor, the intermediate pair of apertures being aligned along a central axis of the anchor, and each of the two central pairs of apertures offset from the central axis and disposed on opposing sides of the central axis;
- a cradle at the other end thereof, configured for looping around a graft; and
- an adjustable length of suture disposed therebetween, the suture extending through the two central pairs of apertures so as to form a first and a second suture loop;
- wherein the cradle defines a sleeve portion through which first and second ends of the suture are threaded in opposite directions to cross over each other within the sleeve portion and emerge at opposite ends of the sleeve portion; and
- wherein the first and second ends of the suture are passed through separate ones of the intermediate pair of apertures and joined together to form a single tail such that pulling on the single tail draws the cradle towards the anchor, keeping the cradle and thereby the graft centered relative to the anchor.

* * * * *